United States Patent [19]

Kaplan et al.

[11] 4,031,893

[45] June 28, 1977

[54] HYPODERMIC INJECTION DEVICE HAVING MEANS FOR VARYING THE MEDICAMENT CAPACITY THEREOF

[75] Inventors: Sheldon Kaplan, Potomac; George B. Calkins; Stanley J. Sarnoff, both of Bethesda; N. Lawrence Dalling, Wheaton, all of Md.

[73] Assignee: Survival Technology, Inc., Bethesda, Md.

[22] Filed: May 14, 1976

[21] Appl. No.: 686,636

[52] U.S. Cl. ..................... 128/218 F; 128/218 P
[51] Int. Cl.² ............................ A61M 5/00
[58] Field of Search ........ 128/218 F, 218 R, 218 P, 128/218 PA, 218 D, 218 DA, 218 A, 215, 216, 234, 220, 221

[56] References Cited

UNITED STATES PATENTS

| 858,025 | 6/1907 | Reese | 128/218 P |
|---|---|---|---|
| 2,902,034 | 9/1959 | Simmonds | 128/218 P |
| 3,400,716 | 9/1968 | Schultz | 128/216 |
| 3,548,824 | 12/1970 | Carr | 128/218 P |
| 3,742,948 | 7/1973 | Post et al. | 128/218 F |
| 3,882,863 | 5/1975 | Sarnoff et al. | 128/218 F |
| R17,059 | 8/1928 | Hein | 128/218 P |

FOREIGN PATENTS OR APPLICATIONS

| 19,848 | 8/1912 | United Kingdom | 128/218 P |

*Primary Examiner*—John D. Yasko
*Attorney, Agent, or Firm*—Witherspoon, Lane & Hargest

[57] ABSTRACT

A hypodermic injection device comprising a cartridge holder having a cylindrical body open at one end and closed at the other end, the closed end being provided with an aperture, a cartridge with the holder, the cartridge including an ampoule having a cylindrical sleeve open at one end and having a necked portion at the other end to receive a hub mounting a cannula, the cannula facing the apertured end of the cylindrical body, a piston slidably carried within the sleeve adjacent the open end thereof to define a medicament chamber between the piston and cannula, fluid medicament in the medicament chamber, the piston having a concave face on the side forming one end of the medicament chamber, a spring power assembly adjacent the open end of the ampoule sleeve for moving the cartridge forward and for injecting the fluid medicament, spacer means positionable between the outer face of the piston and the adjacent spring power means to vary the position of the piston within the ampoule sleeve and thereby control the volume of the medicament chamber and the medicament carried therein, a safety assembly for controlling actuation of the spring power assembly, and a resilient sheath covering the cannula to maintain the cannula in sterile condition.

6 Claims, 3 Drawing Figures

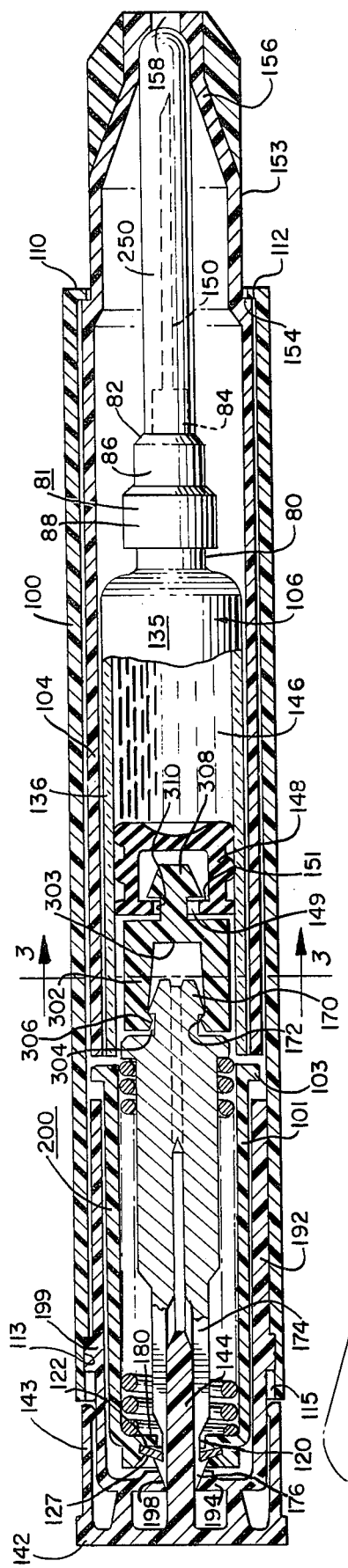

HYPODERMIC INJECTION DEVICE HAVING MEANS FOR VARYING THE MEDICAMENT CAPACITY THEREOF

SUMMARY OF THE INVENTION

This invention relates to injection devices of the gun type wherein spring power means drives an ampoule and cannula to insert the cannula and then inject the medicament. The cannula is provided with a resilient sheath to maintain the cannula in sterile condition at all times prior to injection. Means are also provided to vary the medicament capacity of the ampoule.

In the device of this invention, the ampoule and attached cannula are slidably carried in a cylinderical holder which is closed at one end housing the cannula except for an aperture through which the cannula passes when the unit is actuated. A spring power assembly drives a plunger which drives tha ampoule and cannula forward causing the cannula to travel out through the aperture in the closed end of the cylindrical holder and to enter the locus which is to receive the fluid medicament. Continued movement of the plunger, after placing of the cannula in the locus, forces the piston in the ampoule forwardly to inject the medicament. During this action, the resilient sheath positioned on and over the cannular is held within the closed end of the cylindrical holder and is pierced by the end of the cannula as it proceeds forwardly. As the cannula continues forward, the sheath is compressed between the closed end of the cylindrical holder and the cannula hub. This action continues until the cannula is fully extended, at which time the sheath is not quite fully compressed, thus making it possible for the sheath to act as a shock absorber at all times during forward travel of the cannula. Toward the end of injection, the forward travel of the power spring is such that its energy is less than that now stored in the compressed sheath. Therefore, a slight retraction of the cannula occurs during the terminal portion of the injection. Spacer means is placed between the outer face of the ampoule piston and the plunger to vary the capacity of the medicament chamber.

In view of the foregoing, it is an object of this invention to provide a gun type injection device with means to vary its medicament capacity.

It is another object of this invention to provide such means for varying the medicament capacity in such manner that the addition of a spacer member is all that is required.

It is yet another object of this invention to provide spacer means between the ampoule piston and the plunger to vary the capacity of the ampoule.

It is another object of this invention to provide a spacer member so sized that it will prevent breakage of the ampoule by the plunger.

It is another object of this invention to provide the piston with a concave forward face to enhance sealing qualities of the piston.

It is a still further object of this invention to provide a very simple and inexpensive spacer means for accomplishing the requisite medicament capacity variation.

IN THE DRAWINGS

FIG. 1 is a longitudinal view of the hypodermic injection device of this invention with the important structural details shown in cross section, FIG. 2 is an exploded perspective view illustrating the positioning of the spacer means between the ampoule piston and the plunger, and FIG. 3 is a cross sectional view taken along lines 3—3 of FIG. 1.

DETAILED DESCRIPTION OF THE INVENTION

This application is an improvement of U.S. Pat. No. 3,882,863 issued May 13, 1975, and that disclosure is by reference incorporated herein.

The single embodiment of this invention illustrated in FIGS. 1-3 is merely one example of the injection apparatus that can advantageously use the spacer arrangement of this invention.

The device comprises an outer cylindrical sleeve 100 having an inturned shoulder 110 at one end and an annular groove 113 in the inner wall adjacent the other open end. A cartridge assembly 106 is assembled in the shouldered end of the outer sleeve 100. The cartridge assembly 106 includes a cartridge holder sleeve 104 fitted within the sleeve 100 and having a decreased forward end portion 153 forming a shoulder 154 which fits against seat 112 provided by outer sleeve shoulder 110. The extreme forward end portion 156 of the holder sleeve 104 is tapered to form a small circular aperture 158.

The cartridge 135 includes an ampoule cylinder 136 with liquid medicament 146 therewithin and a piston 148 at one end with a cannula 150 at the other end. The piston 148 is provided with a concave forward face 147 so that when the piston moves toward the cannula 150 pressure of the medicament on the concave face 147 will produce an outward expansion of the piston periphery adjacent thereto to enhance the piston seal. The ampoule cylinder 136 has a necked portion 80 with a diameter less than that of the cylinder 136 and terminates in an enlarged annular flange 133. The cannula 150 is secured to a cannula hub 81 which in turn is affixed to the enlarged flange 133 on the necked portion 80. More specifically, cannula hub 81 comprises a reduced diameter portion 84 which is secured to cannula 150 and an intermediate body 86 connected to enlarge body 88. The enlarged body 88 fits over and is secured to the annular flange 133 of the necked portion 80 of the ampoule cylinder. Within the necked portion 80 of the ampoule cylinder 136, between the inner end of the cannula 150 and the medicament, there may be interposed a fluid pressure rupturable diaphragm generally like that described in U.S. Pat. No. 3,391,695 to Sarnoff.

The cartridge assembly 106 is assembled in the outer sleeve 100 with the cannula 150 spaced from the apertured end of the holder 104. The overall length of the ampoule 135 and cannula is such that it is all contained within the holder sleeve 104, as illustrated in FIG. 1.

The outer sleeve 100 is of such length that it accomodates the cartridge assembly 106 in one end and receives the gun assembly 200 in the other to complete the device. The gun assembly 200 comprises an inner gun sleeve 101 having an out turned flange 103 which fits up against the end of the cartridge holder sleeve 104 when the gun assembly is inserted in the outer sleeve 100. The other end of the inner gun sleeve 101 is centrally apertured to form a hole 120. The rear outer face 122 of the inner gun sleeve 101 is planar and perpendicular to the longitudinal axis of the sleeve for a purpose to be brought out later.

A plunger 162 fits within the inner sleeve 101, said plunger comprises four identical longitudinal blades 164 extending radially outward at 90° intervals from a common longitudinal axis. Each blade has a body portion 165 sized such that when in assembled form as a plunger the effective peripheral size will allow smooth fitting within the inner diameter of gun spring 138. The forward end of each blade body portion is provided with an outwardly extending lug 166 adapted to act as a stop for the gun spring 138. A frusto-conical tab 170 extends forwardly from the body portion 165 on each blade 164. Immediately rearward of the tab 170 is a slot 172 such that when all blades are assembled in the described manner a peripheral size is developed which is substantially less than that formed by the frusto-conical tabs 170 to provide a locking arrangement.

The rearward end of each blade 164 has a cut out portion on its underside to thus form an elongated finger 174 terminating in a frusto-conical detent 176 sloping rearwardly. A notch is formed immediately forward of the detent 176 to provide a square locking face 178.

Referring to FIG. 1, gun spring 138 is positioned over the plunger 162 with one end abutting lugs 166 and the other end bearing against the inner face 180 of the end wall of the inner sleeve 101. The gun spring is thus in compressed condition. In this position the spring 138 is held in compression by the detents 176 which have been carried inwardly by engaging the periphery of the end wall of opening 120 and pass therethrough whereupon the square faces 178 of the detents 176 come to rest on the planar face 122 of the end wall of the inner sleeve 101. Where desired, the rear planar face 122 may be overlaid with a metal washer 127 for added strength in the stressed area.

As will be apparent from FIG. 1, the tabs 170 could connect the plunger to piston 148 by introduction of the tabs 170 into piston aperture 149. Such an arrangement would provide maximum medicament capacity. If a medicament dose of something less than maximum is dictated then a spacer 300 should be placed between the plunger 162 and the piston 148 to thereby push the piston forward in the ampoule cylinder 136 to change the size of the medicament chamber. Even with the employment of spacers of various sizes, it will be unnecessary to change the size or operation of any element of the hydpodermic injection device.

The spacer 300 comprises a cylindrical body 302 having a closed end 303 and an open end 304 which has a radially and inwardly projecting V-shaped portion 306 spaced from the open end 304, said portion 306 being adapted to frictionally engage the tabs 170 of the plunger 162. There is a frusto-conical retainer 308 extending from the closed end of the spacer 300. This retainer has a peripheral recess 310 immediately rearward of the retainer 308. A plurality of longitudinal ribs 312 extend radially from the body and are equally spaced around the periphery thereof. The effective outside diameter of the spacer 300 as produced by the aforementioned ribs 312 is slightly less than the inner diameter of the ampoule sleeve 136 so that the spacer will assist in properly centering the plunger 162. See FIG. 3 of the drawings. This is quite important since the gun spring 138 when released exerts a substantial force on the plunger 162 such that if the plunge strikes the glass ampoule some type of breakage will very likely take place and cause improper operation of the device.

As shown in FIG. 1, the spacer 300 is assembled in the device by forcing the frusto-conical tabs 170 of the plunger 162 into the spacer end aperture 304 so that the tabs 170 frictionally engage the V-shaped portion 306, thus the plunger 162 is connected to the spacer. The spacer retainer 308 is forced into the piston opening 149 so that the retainer slop 310 will fit over the adjacent shoulder 151 on the piston 148 to operatively connect the spacer 300 to the piston 148.

Referring to the rearward end portion of the device, an outer gun sleeve 192 fits over inner gun sleeve 101 and has a closed end 194 with a central aperture from which extends a frusto-conical cam surface 198 sized and shaped to cooperate with frusto-conical detents 176 to cam said detents radially inwardly. The outer gun sleeve 192 is provided with a circumferential locking rib 199 which fits in groove 115 in the outer sleeve 192 to retain the gun assembly 200 in position in the outer sleeve. It should be noted that the length of the outer sleeve 192 is sized with respect to the inner gun sleeve 101 so as to assure that there will be space between the forward ends of the gun sleeves so that they may move longitudinally relative to each other to cam frusto-conical detents 176 inwardly in operating the device.

In order to make certain that frusto-conical detents 176 are not accidentally cammed inwardly, a safety pin assembly is provided. This assembly comprises a cap 142 having a cylindrical sleeve 143 sized to fit over the end portion of the outer gun sleeve 192. A safety pin 144 extends inwardly from the center of the cap 142 into the opening formed by the inner ends of the fingers 174 to thereby prevent inward movement of the detents 176.

As shown in FIG. 1, resilient sheath 250 is positioned over the cannula 150 such that the open end of the sheath fits over and around cannula tab portion 84 and abuts the shoulder 82 formed by hub portions 84 and 86. The length of the sheath is such that is closed end is slightly beyond or spaced from the end of cannula 150.

Upon the actuation of the injection device, the cartridge assembly 106 moves forward whereby the sheath 250 is compressed between the annula end of the cartridge holder sleeve 104 and the hub shoulder 82. The cannula sheath, in being compressed, acts as a shock absorber to gradually absorb some of the energy provided by the power spring 138 as it drives the cartridge assembly 106 forward. It should be noted that at no time, even when the cannula is fully extended, is the sheath compressed to such an extent that it would act as a solid and thereby provide no shock absorbing in such a condition.

When the cannula 150 is fully extended, the cannula sheath 250 will be compressed the greatest amount hence the largest reactionary force will exist in the compressed sheath in such position. When the cartridge 135 has completed its travel under the force of spring 138, the forward movement of piston 148 commences under the action of spring 138 to start the injection sequence. The size of the sheath is such that in the maximum compressed condition the forces stored in the sheath are greater than those in spring 138 when it has reached a point just short of full piston travel. At this point the compressed sheath 250 takes over and causes the cartridge 135 and attached cannula 150 to retract slightly, while the last stage of injection takes place. It is at this stage that the forces of the compressed sheath and the spring 138 are counterbalanced.

The advantages of using a spacer 300 in the described combination have been mentioned earlier, the most important being the ability to vary the capacity of the medicament chamber by controlling the positioning of the piston 148 in the ampoule cylinder 136. This is accomplished by means of spacer 300. Thus by having a supply of spacers of various lengths, the assembler and filler of the devices may selectively determine the medicament capacity of the unit. The fact that the addition or revision of other components of the unit is not required makes this invention particularly attractive. The economics possible by this invention will be significant.

Additionally, the spacer provides protection for the glass ampoule since it is provided with external longitudinal ribs 312 which serve to center the spacer and connected plunger so that there will be no danger of ampoule breakage because of plunger contact with the glass ampoule cylinder.

The manner in which the spacer is connected to the plunger and piston is significant since assembly is greatly simplified by such arrangement. The spacer is generally made from an appropriate plastic which qualifies both from a production and use standpoint, one of such plastics being polyethylene.

What is claimed is:
1. In a hypodermic injection device comprising a gun, a cartridge holder in operative relationship to the gun, a cartridge within the holder, said gun comprising a sleeve open at one end thereof, a plunger positioned within the sleeve, spring power means acting on said plunger tending to move it out the open end of the sleeve, restraining means cooperating with said plunger to prevent plunger movement, safety means acting on said restraining means to render it inoperative, said cartridge holder comprising a hollow shell acting as a prolongation of the gun sleeve, said cartridge including an ampoule comprising a hollow cylindrical sleeve, a piston slidably positioned in one end thereof and means mounting a cannula extending from and closing off the other end, a medicament chamber formed between the piston and the cannula, the cartridge fitting within the cartridge holder with the free end of the cannula within the end of the holder remote from the gun, a resilient sheath covering the cannula to maintain the cannula in sterile condition, the improvement comprising:
 means positioned between the outer face of the piston and the adjacent end of the plunger to control the position of the piston within the ampoule sleeve thus determining the volume of the medicament chamber and thus the quantity of medicament carried in the syringe.
2. The invention as set forth in claim 1 and wherein the means positioned between the outer face of the piston and the adjacent end of the plunger is a spacer member.
3. The invention as set forth in claim 2 and wherein the spacer is a cylindrical member having means on each end thereof for connection to the outer face of the piston and the adjacent end of the plunger.
4. The invention as set forth in claim 3 and wherein the spacer is a cylindrical member having longitudinally running ribs extending radially outward from the axis and the cylinder.
5. The invention as set forth in claim 4 and wherein the peripheral size of the spacer is such that it will freely ride within the ampoule sleeve and prevent damage thereto by the plunger.
6. The invention as set forth in claim 1 and wherein the piston has a concave face on its cannula side so that pressure of the medicament upon operation of the device will cause the piston periphery adjacent the cancave face to expand outwardly to provide a better seal.

* * * * *